US012318515B2

(12) United States Patent
Balluff et al.

(10) Patent No.: US 12,318,515 B2
(45) Date of Patent: Jun. 3, 2025

(54) TEMPERATURE-CONTROL DEVICE AND TEMPERATURE-CONTROL METHOD (71) Applicant: Barkey GmbH & Co. KG, Leopoldshoehe (DE)

(72) Inventors: Michael Balluff, Bielefeld (DE); Harry Rempel, Leopoldshoehe (DE); Christian Petrach, Vlotho (DE)

(73) Assignee: Barkey GmbH & Co. KG, Leopoldshoehe (DE)

( * ) Notice: Subject to any disclaimer, the term of this patent is extended or adjusted under 35 U.S.C. 154(b) by 626 days.

(21) Appl. No.: 17/056,131

(22) PCT Filed: Apr. 3, 2019

(86) PCT No.: PCT/DE2019/100306
§ 371 (c)(1),
(2) Date: Nov. 17, 2020

(87) PCT Pub. No.: WO2019/223828
PCT Pub. Date: Nov. 28, 2019

(65) Prior Publication Data
US 2021/0220534 A1 Jul. 22, 2021

(30) Foreign Application Priority Data
May 22, 2018 (DE) ..................... 10 2018 112 194.6

(51) Int. Cl.
*A61M 1/02* (2006.01)
*A61M 5/44* (2006.01)
(Continued)

(52) U.S. Cl.
CPC .......... *A61M 1/0281* (2013.01); *A61M 5/445* (2013.01); *H05B 1/0244* (2013.01);
(Continued)

(58) Field of Classification Search
CPC ... A01N 1/02; A61J 3/00; A61M 1/02; A61M 1/0281; A61M 2202/0415;
(Continued)

(56) References Cited

U.S. PATENT DOCUMENTS 6,748,164 B1   6/2004  Kuzyk
6,861,624 B1   3/2005  Pelster
(Continued)

FOREIGN PATENT DOCUMENTS

DE    3047784 A1    7/1982
DE    19730994 A1   2/1999
(Continued)

OTHER PUBLICATIONS

International Search Report issued on Oct. 14, 2019, in International Application No. PCT/DE2019/1000306.
(Continued)

Primary Examiner — John J Norton
Assistant Examiner — Theodore J Evangelista
(74) Attorney, Agent, or Firm — Patent Central LLC; Stephan A. Pendorf (57) ABSTRACT A device for controlling the temperature of and thawing a temperature-controlled product, with a housing containing the temperature-controlled product, a heating module for introducing heat at least at one side of the temperature-controlled product and an actuating member, using which movement can be introduced into the temperature-controlled product. The actuating member is designed as a mechanical actuating element which extends along and ideally makes direct contact with the temperature-controlled product, and which can be controlled such that it executes a periodic and/or non-periodic movement.

18 Claims, 9 Drawing Sheets (51) Int. Cl.
  *H05B 1/02* (2006.01)
  *H05B 3/22* (2006.01)
(52) U.S. Cl.
  CPC ..... *H05B 1/025* (2013.01); *A61M 2202/0415* (2013.01); *A61M 2205/3368* (2013.01); *A61M 2205/3653* (2013.01); *H05B 3/22* (2013.01)
(58) Field of Classification Search
  CPC . A61M 2205/3368; A61M 5/44; F28D 21/00; H05B 1/00; H05B 1/0244; H05B 1/025; H05B 3/22
  See application file for complete search history.

(56) References Cited

U.S. PATENT DOCUMENTS

| | | | |
|---|---|---|---|
| 8,012,416 B2 | 9/2011 | Kuzyk | |
| 2015/0122793 A1* | 5/2015 | Takizawa | H05B 1/0294 219/255 |
| 2019/0075786 A1* | 3/2019 | Milne | B01L 7/00 |

FOREIGN PATENT DOCUMENTS

| | | |
|---|---|---|
| DE | 10033025 A1 | 1/2002 |
| EP | 0318924 B1 | 3/1992 |
| JP | 2936108 B2 | 8/1999 |
| WO | 2014125660 A1 | 8/2014 |
| WO | 2016023034 A1 | 2/2016 |
| WO | 2017153761 A1 | 9/2017 |

OTHER PUBLICATIONS

German Search Report issued on Jan. 31, 2019, in German Application No. 10 2018 112 194.6.
Partial Search Report issued on Jul. 19, 2019, in International Application No. PCT/DE2019/100306.
International Preliminary Report on Patentability issued on Nov. 24, 2020, in International Application No. PCT/DE2019/1000306.

* cited by examiner

TEMPERATURE-CONTROL DEVICE AND TEMPERATURE-CONTROL METHOD

The invention relates to an apparatus for controlling the temperature of and thawing a temperature-controlled product, comprising a housing, containing the temperature-controlled product, a heating module for introducing heat to at least one face of the temperature-controlled product, and an actuator, by means of which the temperature-controlled product can be moved.

The invention further relates to a method for controlling the temperature of and thawing a temperature-controlled product, in which heat is introduced to the temperature-controlled product while a compressive force is exerted on part of the temperature-controlled product in a specified time interval by means of an actuation element.

U.S. Pat. No. 6,748,164 B1 discloses an apparatus for thawing a temperature-controlled product, in which the temperature-controlled product is surrounded by a heating member. In the heating member, a warm liquid is circulated. By the direct thermal contact between the heating member and the temperature-controlled product, heat is transferred from the heating member to the temperature-controlled product. A housing base, which can be periodically moved up and down and on which the heating member is arranged, is provided as an actuator for accelerating the thawing process. The heating member is thus made to perform a pivoting movement, wherein a pivot axis extends along an edge of the heating member. The temperature-controlled product is thus indirectly pivoted, wherein an edge side is arranged close to the pivot axis.

U.S. Pat. No. 8,012,416 B2 discloses an apparatus for thawing a temperature-controlled product, wherein opposite faces of the temperature-controlled product are each in contact with a heating element. The lower heating member is arranged on a plurality of support plates, each of which is associated with an inflatable pillow. The pillows are anticyclically inflated in such a way that one half of the heating member and then the other half of the heating member are lifted in relation to a center plane. This allows the temperature-controlled product to be compressed firstly on a first half and then on a second half in relation to the center plane. The drawback to the known apparatus is that it is relatively costly to temporarily compress part of the temperature-controlled product. The frequency and acceleration are relatively limited.

EP 0 318 924 B1 discloses an apparatus for controlling the temperature of and thawing a temperature-controlled product, in which the temperature-controlled product is arranged between two heating members of a heating module. The heating members are configured as plastics bags in which a warm liquid is circulated by a pump. On edges of the heating members, a crank is arranged, which is rotated by a motor and alternately compresses edges of the upper heating bag and the lower heating bag such that the warm liquid inside the heating bags is moved away from the crank. This results in movement oscillations within the heating bag that can be transferred to the temperature-controlled product.

The object of the present invention is to further develop an apparatus for controlling the temperature of and thawing a temperature-controlled product such that the effectiveness of the temperature control is further improved in a simple manner.

To achieve said object, the invention is, in conjunction with the preamble of claim 1, characterized in that the actuator is configured as a mechanical actuation element which extends in ideally direct contact with the temperature-controlled product and which can be actuated so as to perform a periodic and/or non-periodic movement.

On account of the direct contact of a mechanical actuation element with the temperature-controlled product, the apparatus according to the invention allows movement of the temperature-controlled product to be controlled in a direct, targeted manner such that the transfer of heat from the heating member to the temperature-controlled product can be accelerated. Advantageously the movement dictated by the actuation element can be directly and indirectly transferred to the temperature-controlled product. Undesired disturbance caused by other components during the transfer of movement from the actuation element to the temperature-controlled product can be avoided. In particular, the invention allows a typically heated part of the temperature-controlled product that is located in an outer region to be relatively quickly exchanged with a typically cool part of the temperature-controlled product that is located in a core region thereof. This ensures relatively fast mixing of the temperature-controlled product. The temperature-controlled product can be configured as a fluid or gel arranged in outer packaging, for example. The invention thus allows the fluid or gel to be mixed relatively quickly. The temperature-controlled product can be heated by conduction or by radiation (infrared radiation, microwave) or by air flow. According to the invention, the mechanical actuation element is mechanically directly coupled to the temperature-controlled product. In this way, preferably a sudden movement impulse can be directly applied to part of the temperature-controlled product.

According to a preferred embodiment of the invention, the mechanical actuation element can be actuated such that a pivoting movement is performed. In the process, the temperature-controlled product is partly deflected from the plane of extension thereof in different paths. The temperature-controlled product is deformed or "kneaded", which leads to internal flow or movement of the frozen core and the already thawed portion of the temperature-controlled product. The pivot axis preferably extends in the region of a center plane or transverse center plane of the temperature-controlled product such that the temperature-controlled product is pivoted back and forth about the center axis thereof in the manner of a paddle of a rowing boat. Advantageously, the frozen part of the temperature-controlled product and the already thawed portion thus can be constantly moved in a back-and-forth movement in the already molten part of the temperature-controlled product. This results in inhomogeneous flow within the temperature-controlled product, wherein cold liquid flows to the surface of the temperature-controlled product, which results in a higher temperature gradient from the heating element to the temperature-controlled product. It has been demonstrated that this allows a 30% reduction in the thawing time.

According to a preferred embodiment of the invention, the mechanical actuation element has an areal or flat design. Said actuation element can be formed to suit to the shape of the temperature-controlled product, thus establishing linear and/or flat contact between the actuation element and the temperature-controlled product. Preferably, the actuation element has a flat design such that said actuation element can be positioned in a space-saving manner between the temperature-controlled product and the heating member.

According to a further development of the invention, the actuation element is configured as a rod element comprising a plurality of rods that surround an opening. The opening allows direct contact of the heating member with the temperature-controlled product, with only a minimal reduction in the surface area of heat transfer between the heating member and the temperature-controlled product compared to an apparatus without the actuation element.

According to a further development of the invention, the actuation element has a periphery that is adjusted to the periphery of the temperature-controlled product. The adjustment to the size of the temperature-controlled product allows the pivoting movement to be performed with relatively little exertion of force.

According to a further development of the invention, the actuation element is coupled to an actuator, in particular a stepper motor, the actuator actuating the actuation element such that the actuation element is periodically or non-periodically pivoted back and forth between a maximum and a minimum actuation angle. The pivoting movement is preferably of a constant amplitude. The actuator can also be configured as a magnetic or pneumatic member, instead of a motor. This results in a cyclic or uniform back-and-forth movement or paddle movement of the temperature-controlled product about the pivot axis. Alternatively, said movement can also be performed at an amplitude that is variable with time.

According to a further development of the invention, the actuation element can be actuated so as to be continuously pivoted at a frequency of 0.1 to 25 Hz. It has emerged that the best temperature control results are achieved in said frequency range. The shortening of the thawing time is in particular achieved by the impulsive cyclic or anticyclic action of an impact force on multiple parts of the temperature-controlled product. For this purpose, the actuation element acts on the temperature-controlled product at different points thereof at a high acceleration.

According to a further development of the invention, the actuation element is actuated so as to perform a linear movement and/or pivoting movement at an amplitude in the range of +/−2 mm to +/−100 mm, for example +/−10 mm to +/−30 mm, preferably +/−25 mm. It has been demonstrated that even these relatively small deflections lead to a strong temperature control result.

According to a further development of the invention, rods of the rod element are formed of a wire material. Advantageously, the metal wire allows a minimal loss of the surface area of heat transfer. The low mass of the wire material also results in only a limited loss of the heating capacity of the rod element itself. As a result of a rigid or stable design of the wire material, fast movements and high acceleration acting directly on the temperature-controlled product can be achieved. If the heating member is configured as a liquid pad, it is possible to mix or stimulate not only the temperature-controlled product, but also the liquid pad at the same time. Thus, the actuation element can be easily produced. Said actuation element has a rigidity that is sufficient for the intended use.

According to a further development of the invention, a plurality of rod elements can also be arranged along a pivot axis. Advantageously, this allows a plurality of smaller enclosed areas to be formed, by means of which the pivoting movement is transferred directly to the temperature-controlled product.

According to a further development of the invention, the heating member can be configured as a temperature-control pad or a gel pad, the contents of which are electrically heated. Alternatively, the heating member can also be configured as a plastics bag containing a liquid, temperature-controlled medium, the medium being circulated by a pump.

The actuation element according to the invention can be universally used, irrespective of the functionality of the heating member.

To achieve the object, the invention is, in conjunction with the preamble of claim 18, characterized in that a duration of action, a size of action and/or an intensity of action of the actuation element is changed on the basis of a specified point in time of the temperature-control process and/or an operating or process parameter of the temperature-controlled product.

An example embodiment of the invention is described below in more detail on the basis of the drawings, in which.

It shows.

Figure 1:
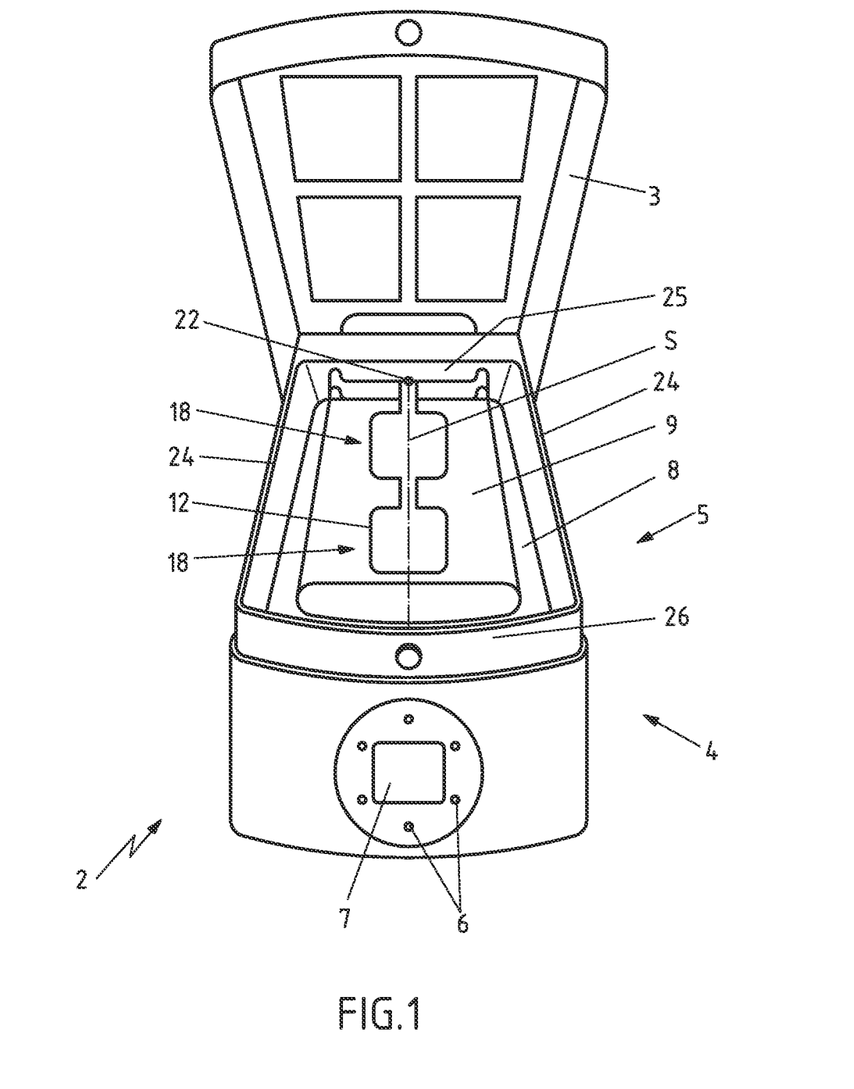
FIG. 1 is a perspective front view of a temperature-control device, with an opened lid, wherein a heating element and a mechanical actuation element above are arranged on a base of the housing.

An apparatus according to the invention for controlling the temperature of and thawing a temperature-controlled product 1 comprises a housing 2, the upper side of which is configured as a hinged lid 3. Inside the housing 2, a lower base chamber 4 is provided, within which an electrical control unit and other units for allowing temperature control are arranged in a temperature-control chamber 5 arranged above the base chamber 4. At the level of the base chamber 4, the housing 2 has operating elements 6 and a display unit 7 on the front, such that the thawing device comprised by the housing 2 can be operated by a person.

The temperature-control chamber 5 has a fixed base 8, which, at the same time, forms a partition wall with respect to the base chamber 4. The heating member consists, inter alia, of the first heating element 9 located on the base 8 and an associated heating module 10 located in the base chamber 4. At the level of an upper face 11 of the lower heating element 9, a mechanical actuation element 12 is arranged. In the operating state of the thawing device, in which the lid 3 is closed, the temperature-control chamber 5 has the vertical layered structure shown in FIG. 3. The temperature-controlled product 1 is adjacent, in the upward vertical direction, to the first actuation element 12. A second upper actuation element 13 is located above the temperature-controlled product 1. A second heating element 14 of the heating module 10 is located above the second actuation element 13. The temperature-control chamber 5 is ideally of a symmetrical structure with respect to a longitudinal center plane $L_T$ of the temperature-controlled product 1. An actuation element 12, 13 and an adjacent heating element 9, 14 are arranged on both sides of the temperature-controlled product 1.

Figure 3:
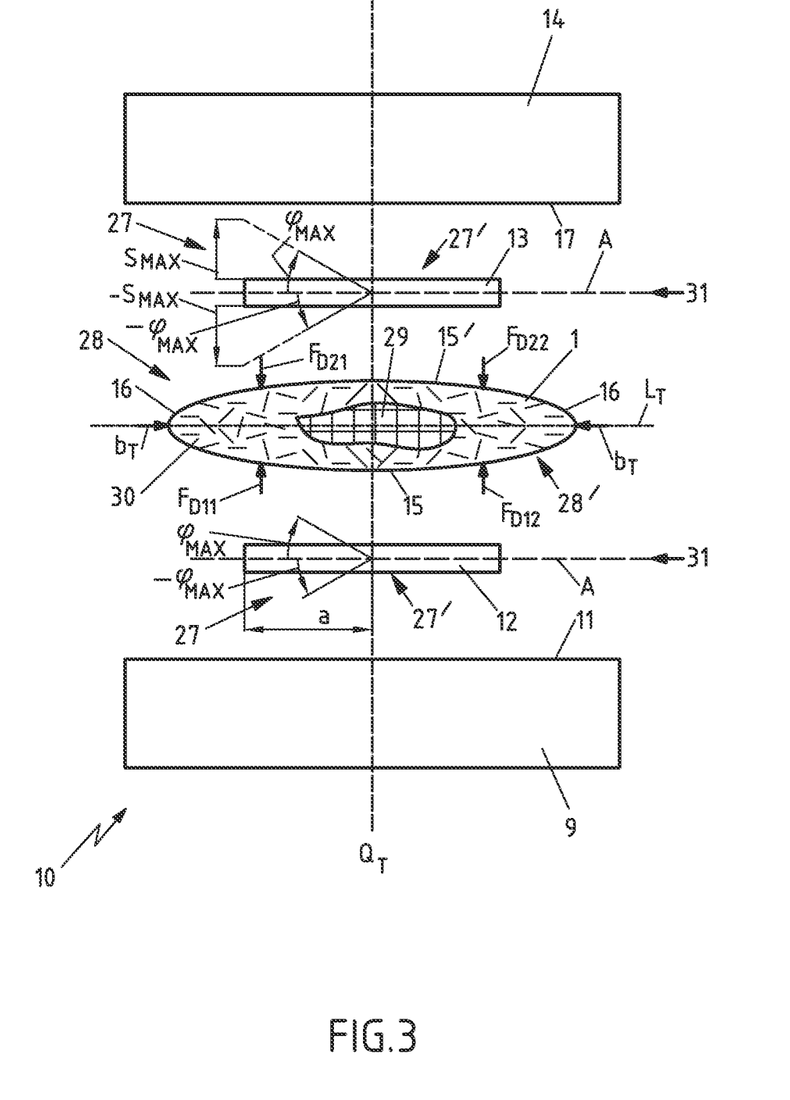
FIG. 3 is an exploded view, in vertical section, of the components arranged in a temperature-control chamber of the temperature-control device.

The temperature-controlled product 1 comprises, for example, a plasma or blood material surrounded by a bag as outer packaging. Ideally, the bags of the temperature-controlled product 1 are relatively flat such that the temperature-controlled product 1 has two opposite faces 15, 15' and narrow peripheral faces 16. The narrow faces 16 connect the opposite faces 15, 15'. The faces 15, 15' are preferably rectangular.

Alternatively, the temperature-controlled product 1 can also be polygon-shaped with faces that are different or of equal size. For example, the temperature-controlled product 1 can also be pear-shaped, cube-shaped, or lump-shaped. In this case, the temperature-controlled product 1 is inserted into the temperature-control chamber 5, wherein it is gripped by the actuation elements 12, 13 and/or the heating elements 9, 14. On account of the preferably flexible design of the temperature-controlled product, at least when said product is in an advanced thawed state, flat faces can be formed such that the surface area of heat transfer is increased in comparison with the original state.

For better illustration, the components in FIG. 3 are spaced apart from one another. Said components are in fact in close contact, one above the other. Thus, the first lower actuation element 12 is in direct, areal/flat contact with the lower face 15 of the temperature-controlled product 1 and the upper face 11 of the first lower heating element 9. The upper second actuation element 13 is in direct, areal contact with the upper face 15' of the temperature-controlled product 1 and a lower face 17 of the upper second heating element 14.

Figure 2:
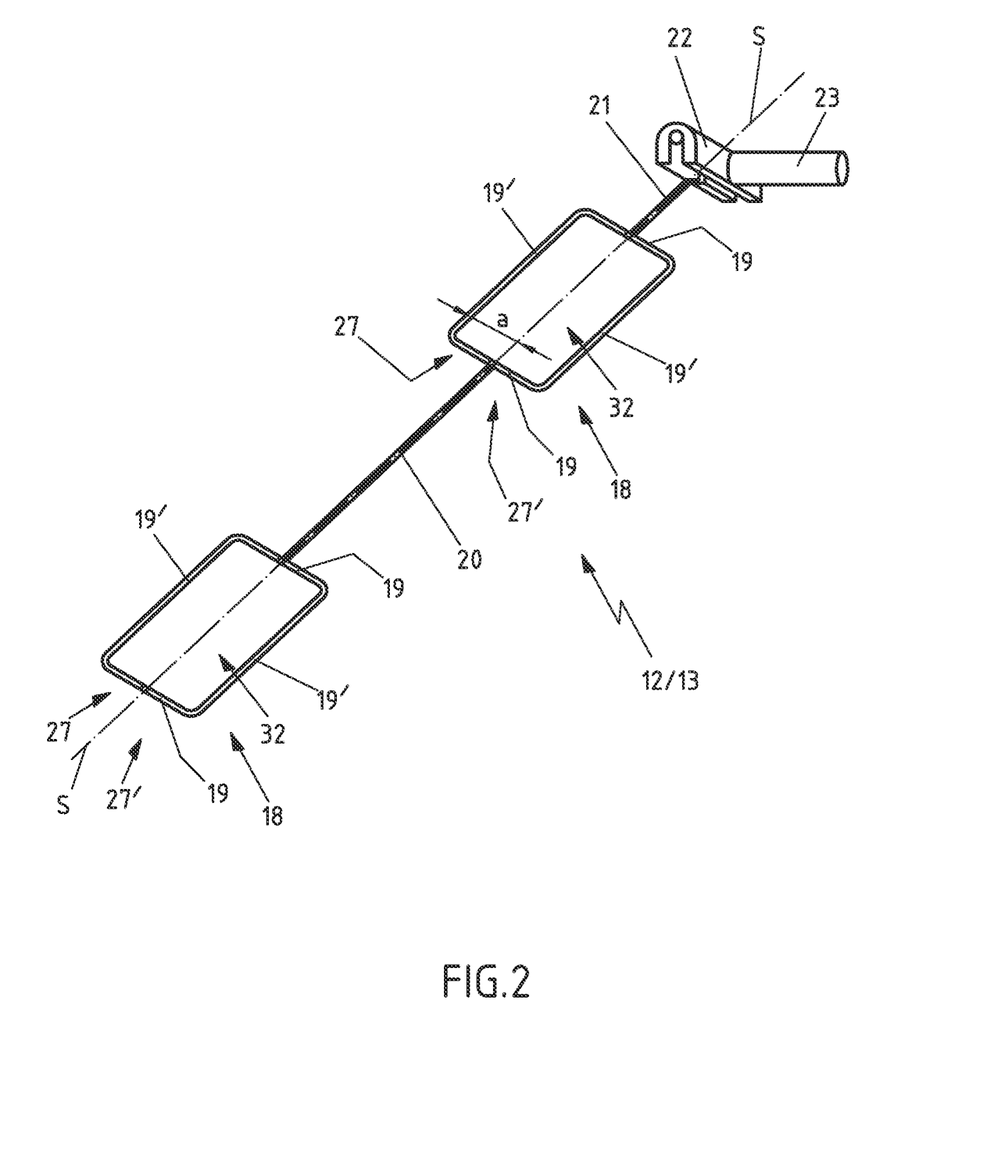
FIG. 2 is a perspective view of an actuation element.

The first actuation element 12 and the second actuation element 13 can preferably be identically designed. Said actuation elements each comprise two paddle portions 18, which are distributed in the longitudinal direction of the actuation element 12, 13 and each consist of a rectangularly extending rod 19. The paddle portions 18 are interconnected by a connecting rod 20. The connecting rod 20 can extend continuously from a first end of the actuation element 12, 13 to a second end thereof. One end of the connecting rod 20 is adjoined by a T-piece 21, which is mounted in a locking manner in a holder 22, for example. For this purpose, the holder 22 has a groove in which a transverse end rod of the T-piece 21 is mounted. The holder 22 is adjoined by a hollow cylinder 23, with which a shaft (not shown) of a motor can be engaged for conjoint rotation. In the operating position, the hollow cylinder 23 or the shaft extends coaxially with the connecting rod 20, which thus extends in a pivot axis S. The motor serves as an actuator. Alternatively, the actuator can also be configured to be pneumatic or magnetic, for example as a lifting magnet or rotary magnets.

The first actuation element 12 and the second actuation element 13 can be periodically and/or non-periodically pivoted between a maximum and a minimum actuation angle $\varphi_{MAX}$, $-\varphi_{MAX}$ by the motor, to which said actuation elements are coupled directly by means of the shaft or by means of a gearing. As can be seen from FIG. 1, the actuation elements 12, 13 are centrally mounted at different levels of the temperature-control chamber 5. The pivot axes S typically extend in parallel with a side wall 24 of the temperature-control chamber 5 and perpendicular to a rear wall 25 and a front wall 26 of the temperature-control chamber 5. In the region of the rear wall 25, the holder 22 of the actuation elements 12, 13 is arranged.

The pivot axes S, about which the actuation elements 12, 13 are mounted so as to be pivotable back and forth, extend along or close to a center plane, specifically a transverse center plane $Q_T$, of the temperature-controlled product 1. A first lateral half 27 of the paddle portion 18 of the actuation elements 12, 13 is therefore associated with a first half 28 of the temperature-controlled product 1. A second lateral half 27' of the paddle portions 18 of the actuation elements 12, 13 is associated with a second half 28' of the temperature-controlled product 1. The two halves 27, 27' and 28, 28' can be arranged symmetrically with respect to the pivot axis S or transverse center plane $Q_T$.

The actuation elements 12, 13, which are arranged offset in the direction of the pivot axis S, are preferably actuated identically such that, for the duration of a half period T/2, the first halves 27 of the paddle portions 18 are rotated through a positive angle $\varphi$ towards $+\varphi_{MAX}$, and the second halves 27' are rotated through a negative angle $-\varphi$ towards $-\varphi_{MAX}$. While the first halves 27 of the actuation elements 12, 13 are pivoted upwards, the second halves 27' thereof are pivoted downwards. A compressive force $F_D$ is thus exerted on the temperature-controlled product 1 on opposite faces 15, 15' and on opposite halves 28, 28'. This allows inhomogeneous flow to be deliberately generated in the temperature-controlled product 1, wherein a frozen core 29 moves back and forth and is surrounded by inhomogeneous flow of the already thawed liquid 30, for example.

This allows a particularly high temperature gradient to be generated. The frozen core 29 is a part of the temperature-controlled product 1 that is located in a core region of the temperature-controlled product 1. The liquid 30 surrounding the core 29 corresponds to a part of the temperature-controlled product 1 that is located in an outer region of the temperature-controlled product 1. At the beginning of the temperature-control process, the temperature-controlled product 1 is in a frozen state, wherein both the outer region and the core region are in a solid physical state, i.e. have a temperature of 0° C. or less. By thawing the outer region of the temperature-controlled product 1 and by means of rapid movement of the temperature-controlled product 1 at high acceleration, the action of the apparatus according to the invention on the temperature-controlled product 1 causes said product to be relatively quickly completely thawed by the time that said product has the desired temperature at the end of the temperature-control process.

As can be seen from FIG. 3, orthogonal projections of the pivot axes S of the actuation elements 12, 13 onto a longitudinal center plane $L_T$ of the temperature-controlled product 1 intersect said product.

The paddle portions 18 of the actuation elements 12, 13 typically have a periphery that is smaller than the periphery of the temperature-controlled product 1.

According to an alternative embodiment of the invention, the paddle portions can also be associated with a plurality of temperature-controlled products 1.

Figure 4:
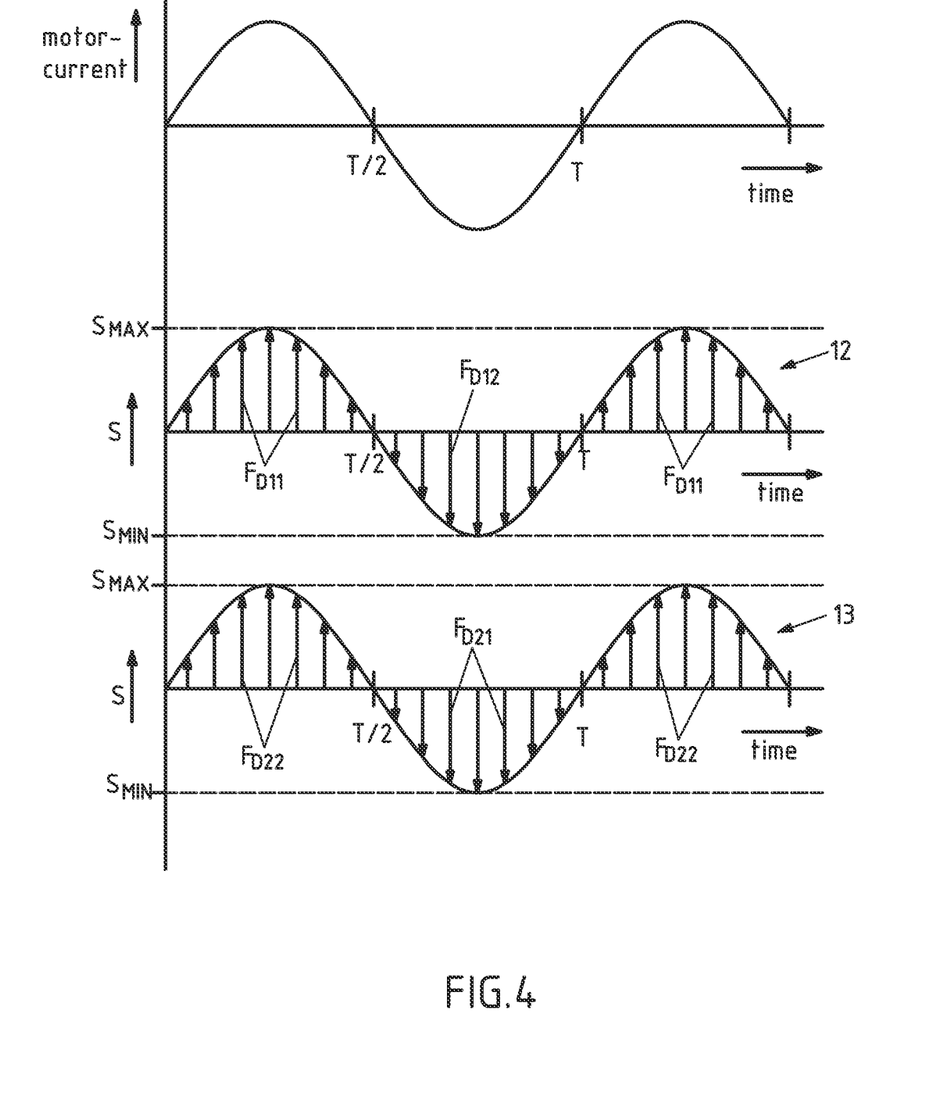
FIG. 4 is an example time chart for a motor and movement of the actuation elements.

As can be seen from FIG. 4, the paddle portions 18 are, in the example, periodically pivoted about the pivot axis S such that an edge rod 19' extending in parallel with the pivot axis S is cyclically subjected to maximum deflection $+/-S_{MAX}$ in relation to a starting position or starting level 31. The starting position 31 extends in a plane parallel to the longitudinal center plane $L_T$ of the temperature-controlled product 1. The maximum deflection $+/-S_{MAX}$ can be in the range of +/−30 mm, preferably in the range of +/−25 mm.

The edge rods 19' are each at a distance a from the pivot axis S, said distance corresponding to 0.2 to 0.7 of a half width $b_T$ of the temperature-controlled product 1.

In the present example embodiment, the mechanical actuation element 12, 13 or the paddle portion 18 is flat.

According to an alternative embodiment of the invention (not shown), the contour of the actuation element 12, 13 or of the paddle portions 18 can also be curved and/or spoon-shaped, for example, in order to be better suited to the shape of the temperature-controlled product 1.

The rods 19, 19' of the paddle portions 18 define an opening 32 into which the flexible temperature-controlled product 1 and/or the heating element 9, 14 can engage in part. This results in direct contact between the temperature-controlled product 1 and the heating element 9, 14 in the region of the opening. Since, according to the present embodiment, the actuation element 12, 13 is configured overall as a rod element, it is possible to establish substantially direct contact between the heating elements 9, 14 and the temperature-controlled product 1.

According to an alternative embodiment of the invention, the paddle portion 18 can also be rigidly or flexibly formed of a heat-conducting material over the entire surface thereof. Optionally, the entire-surface actuation element or paddle portion 18 can consist of multiple rigid segments that are interconnected in the manner of an integral hinge, for example.

The motor pivots the actuation element 12, 13 preferably at a frequency in the range of 0.5 to 5 Hz. Said frequency allows optimum heat input into the temperature-controlled product 1.

The heating elements 9, 14 each comprise a plastics bag in which a liquid, temperature-controlled medium is circulated by a pump (not shown). The pump and heating coils for temperature-controlling the liquid medium are arranged in the base chamber 4.

According to an alternative embodiment of the invention, the heating elements 9, 14 can also be formed by temperature-control pads or gel pads that are individually electrically heated. The required installation space is thus relatively small.

The rods 19, 19' of the actuation element 12, 13 consist of a wire material.

According to an alternative embodiment of the invention (not shown), the thawing device can also comprise only a single actuation element 12, 13 that is arranged either above or below the temperature-controlled product 1. In contrast to the described embodiment, a compressive force $F_D$ is not constantly applied on both faces 15, 15' of the temperature-controlled product 1, but only alternately on a single face 15, 15', specifically on the first face 15 during a first half period T/2 and on the second face 15' during the second half period T/2.

According to one embodiment (not shown), the motor can also be configured as a stepper motor, by means of which the shaft is rotated through a specified angle. The motor curve indicating the motor current I, shown in FIG. 4, will not be sinusoidal in this case.

As can be seen from FIGS. 3 and 4 together, compressive forces $F_D$ are periodically exerted on both faces of the temperature-controlled product 1, i.e. on the first face 15 and the second face 15', by way of example. It is assumed that the actuation elements 12, 13 are pivoted synchronously and/or in the same pivot directions. Thus, when the first half 27 of the paddle portions 18 is pivoted upwards out of the starting position in the plane A, a compressive force $F_{D11}$ is exerted upwards on the temperature-controlled product 1 by the lower actuation element 12, and when the second half 27' of the paddle portions 18 is pivoted downwards, an oppositely directed compressive force $F_{D22}$ is exerted on the temperature-controlled product 1 by the upper actuation element 13. When the actuation elements 12, 13 have reached the maximum deflection $S_{MAX}$ thereof, thus forming the maximum angle $\varphi_{MAX}$ in relation to the plane A of the starting position, a movement reversal takes place such that the compressive forces $F_{D11}$, $F_{D22}$ are eased. When the starting position A is reached after a half period T/2, a compressive force $F_{D12}$ is then exerted on the second half 27' of the lower face 15 by the other halves 27' of the lower actuation element 12, while a compressive force $F_{D21}$ is exerted on the first half 27 of the temperature-controlled product 1 from above by a first half 27 of the upper actuation element 13. In FIG. 4, this is illustrated by corresponding force arrows. The halves 27, 27' of the paddle portions 18 thus function as pivoting levers that have openings. A compressive force $F_D$ is constantly exerted on the lower face 15 and the upper face 15' of the temperature-controlled product 1, the compressive forces $F_{D11}$, $F_{D22}$ and $F_{D21}$, $F_{D12}$ acting on the temperature-controlled product 1 asymmetrically with respect to the transverse center plane $Q_T$.

If just a single actuation element 12, 13 is provided, the compressive forces $F_{D11}$, $F_{D12}$ or $F_{D21}$, $F_{D22}$ are alternately exerted, from only one side, on both halves 28, 28' of the face 15 or 15' of the temperature-controlled product 1 by the halves 27, 27' of the paddle portions 18.

According to an alternative embodiment of the invention (not shown), the two actuation elements 12, 13 can also be actuated so as not to be pivoted in the same direction, but in opposite directions (anticyclically) such that a compressive force $F_D$ is alternately generated in the halves 28 of the lower face 15 and the upper face 15' of the temperature-controlled product 1 and then in the halves 28' of the lower face 15 and the upper face 15' of the temperature-controlled product 1. While the first half 27 of the first actuation element 12 is pivoted upwards, the first half 27 of the second actuation element 13 is pivoted downwards. While the second half 27' of the first actuation element 12 is pivoted downwards, the second half 27' of the second actuation element 13 is pivoted upwards. These contrasting or oppositely directed movements of the actuation elements 12, 13 allow the frozen core 29 and the already thawed components of the temperature-controlled product 1 to be moved more intensely. Advantageously, in this case, the same effect can be achieved with a reduced maximum pivot angle $\varphi_{MAX}$, $-\varphi_{MAX}$ or maximum deflection $S_{MAX}$, $-S_{MAX}$ in comparison with the embodiment having a single actuation element.

Alternatively, the actuation elements 12, 13 can also be periodically and/or non-periodically moved relative to one another in the same direction or in opposite directions such that the deformation force on the temperature-controlled product 1 or on the core 29 and the already thawed surrounding liquid 30 in said product is further increased.

According to one embodiment (not shown), non-periodic movement or non-periodic pivoting movement of the at least one actuation element 12, 13 can be provided, instead of periodic movement.

According to one embodiment (not shown), a time sequence of periodic movement and non-periodic movement of the at least one actuation element 12, 13 can be provided. The actuation element 12, 13 can alternatively also be moved linearly.

According to one embodiment (not shown), the heating element is integrated in the actuation element. Advantageously, the space required can be substantially reduced.

The heating element can be configured, for example, as a temperature-control pad or a gel pad, the contents of which are electrically heated. If the heating element is configured as a plate warmer having rigid heating surfaces, said heating element can simultaneously serve as an actuation element.

Figure 6:
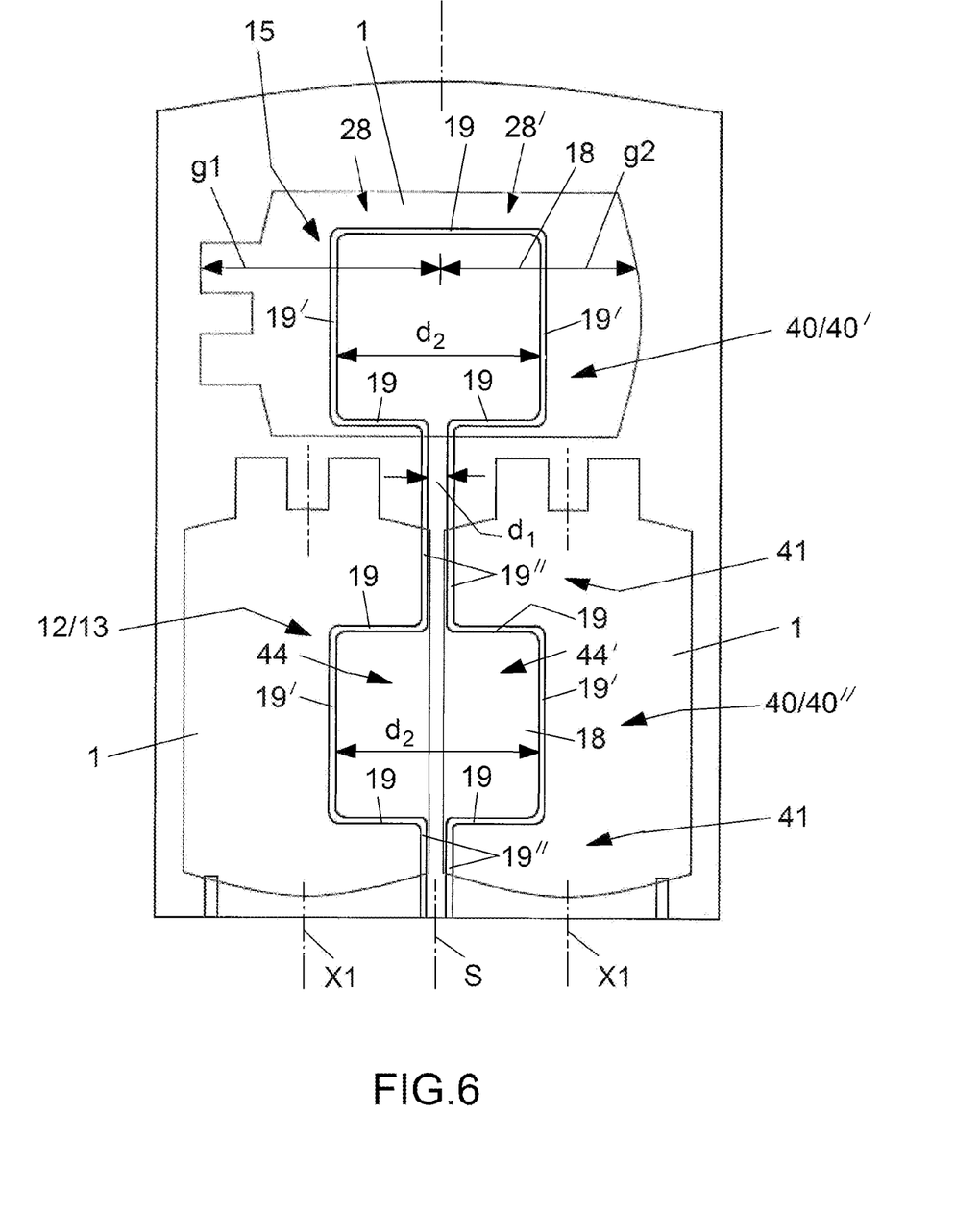
FIG. 6 is a plan view of a temperature-control chamber of the temperature-control apparatus, wherein three temperature-controlled products are associated with the two wide portions of the actuation element, which are arranged offset along the pivot axis.
Figure 7:
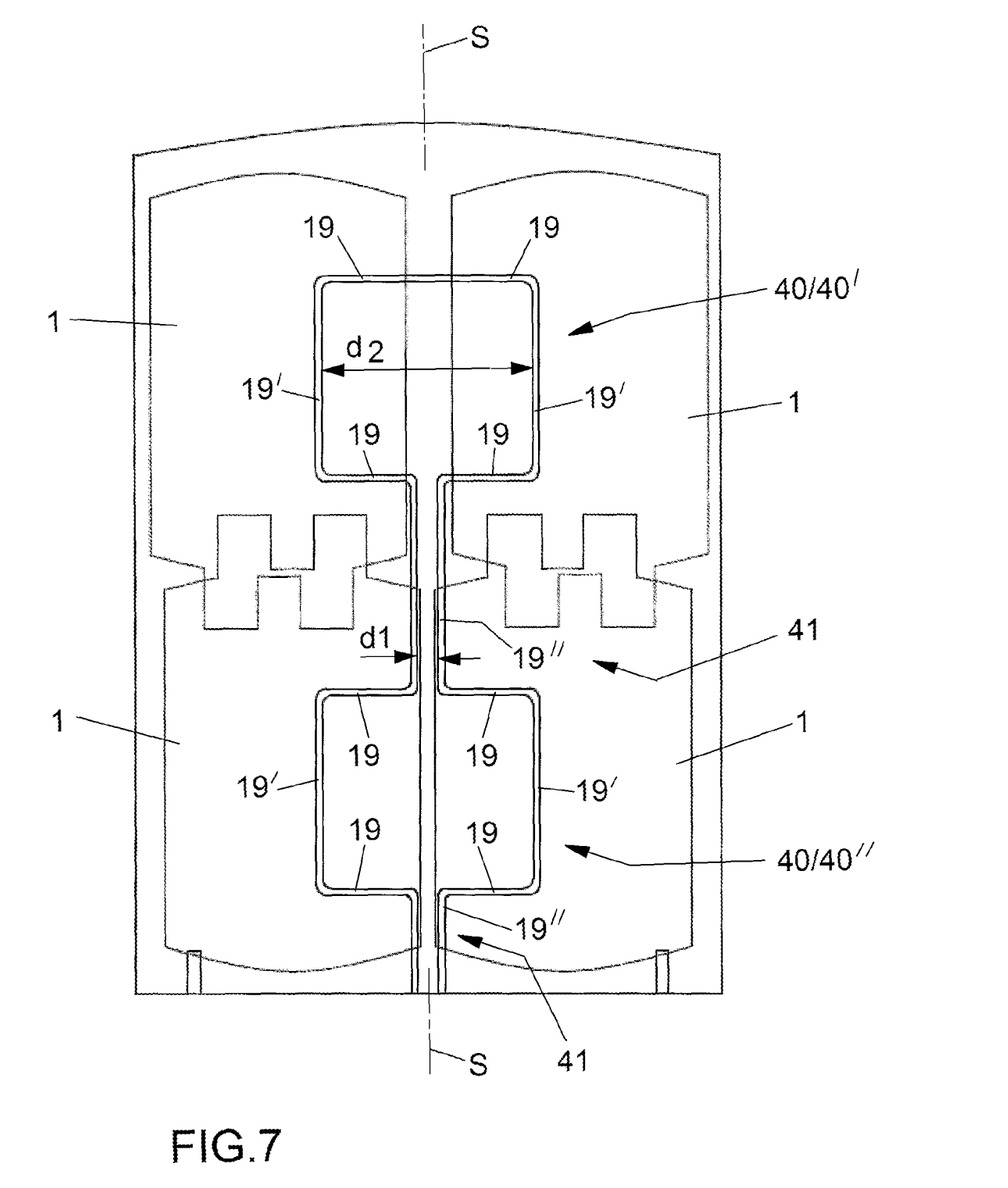
FIG. 7 is a plan view of a temperature-control chamber of the temperature-control apparatus, wherein four temperature-controlled products are associated with the two wide portions of the actuation element, which are arranged offset along the pivot axis.

According to one embodiment of the actuation element according to FIG. 6, which is also shown in FIG. 1, the actuation element 12, 13 consists of a plurality of wide portions 40 and narrow portions 41 that are arranged offset from one another along the pivot axis S. The wide portion 40 of the actuation element 12, 13 includes a pair of edge rods 19' that extend at a relatively large distance d2 from one another. The edge rods 19' extend in parallel with the pivot axis S. The edge rods 19' are adjoined by rods 19 extending substantially perpendicular to the pivot axis S. The edge rods 19' and the adjacent rods 19 form the O-shaped paddle portion 18. The O-shaped paddle portion 18 is configured as an open paddle that has an opening.

In the direction of the pivot axis S, the wide portion 40 is adjoined by the narrow portion 41, which has rods 19'' that extend in parallel with the pivot axis S and are arranged at a relatively small distance $d_1$ from one another. The rods 19'' of the narrow portion 41 extend in the direction of the pivot axis. The rods 19'' of the narrow portion 41 adjoin the rods 19 of the wide portion 40, which extend transversely to the pivot axis, or are coupled to the actuator at one end of the actuation element 12, 13.

As can be seen from FIG. 6, a first wide portion 40' rests against the faces 15, 15' of a temperature-controlled product 1 arranged transversely to the pivot axis S. The first wide portion 40' is adapted to the temperature-controlled product 1 such that the edge rods 19' extend in the range of +/−20%, preferably +/−10%, or alternatively in the vicinity of the centers of gravity or on the centers of gravity of the halves 28, 28' of the temperature-controlled product 1. In the present example embodiment, a distance g1 of the first half 28 is 8 cm, and a distance g2 of the second half 28' is 7 cm. The distance d2 between the edge rods 19' is thus selected such that with reasonable exertion of force, the temperature-controlled product 1 can be deflected about the pivot axis S extending in a transverse center plane $Q_T$ of said product. The lines of action induced by the edge rods 19' on the halves 28, 28' in the direction of the pivot axis S thus extend in the region of the centers of gravity of said halves 28, 28'.

A second, wide portion 40'' of the actuation element 12, 13 acts on two adjacently arranged temperature-controlled products 1. All the temperature-controlled products 1 are arranged in a common plane. A first half 44 of the wide portion 40'' is associated with the second temperature-controlled product 1, and a second half 44' of the wide portion 40'' is associated with the third temperature-controlled product 1. The halves 44, 44' of the wide portion 40'' are arranged symmetrically with respect to the pivot axis S. The edge rods 19' of the halves 44, 44' are each at the same half distance d2/2 from the pivot axis S. The edge rods 19' extend in the region of the centers of gravity of the respective temperature-controlled products 1 or in the vicinity of or in the region of axes of symmetry X1 of the temperature-controlled products 1.

Figure 5:
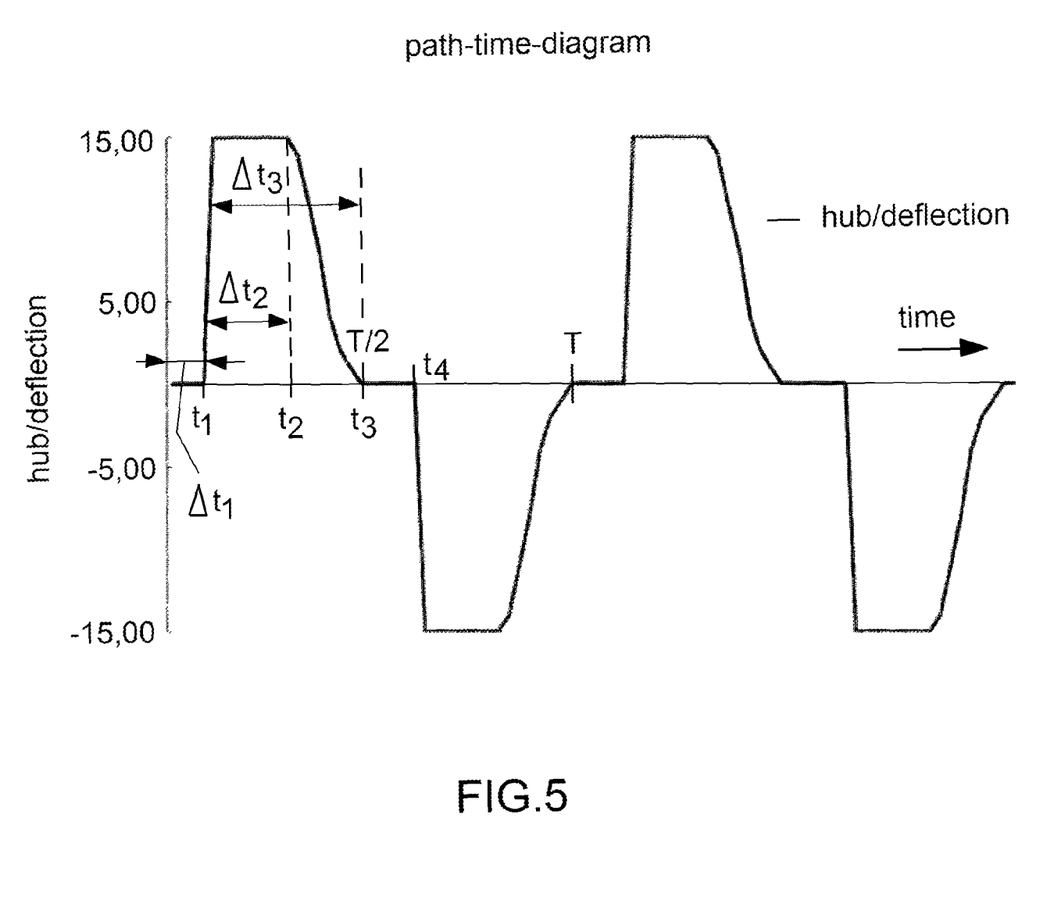
FIG. 5 is an example time chart for deflection of an outer region of a temperature-controlled product or an edge rod of the actuation element.

According to a further embodiment of the invention according to FIG. 5, impulsive deflection of the actuation elements 12, 13 can take place, instead of continuous deflection (harmonic and/or linear oscillation). For example, at the time $t_1$, the edge rod 19' can be suddenly deflected from 0 cm to 15 cm. In a time interval $\Delta t_2$, the actuation element 12, 13 then remains at rest, and at the time t2, said element is subsequently returned suddenly, but at lower acceleration than for the deflection movement in absolute terms, to the starting position again. After reaching the starting position at the time t3, the actuation element 12, 13 remains at rest until a time t4, before the same deflection movement is performed in the other pivoting direction. According to said embodiment, impulsive periodic and/or non-periodic deflections are provided, the actuation element 12, 13 being at rest in the maximum deflection position in the time interval $\Delta t_2$ and in the starting position in the time interval $\Delta t_1$.

The maximum deflection and/or the frequency 1/T and/or the acceleration of the movement of the actuation element 12, 13 can be selected on the basis of the current temperature of the temperature-controlled product 1 in conjunction with a specified threshold temperature or in conjunction with a fixed specified point in time. The actuation elements 12, 13 do not have to be actuated periodically or non-periodically or with the same impulse sequence or with the same deflection curve over the entire running time of the temperature-control process. The extent of deflection or the frequency and the acceleration can be changed depending on the particular temperature-controlled product 1. Different movement profiles can therefore be selected for different temperature-controlled products 1. For example, at the beginning of the temperature-control process, the frequency of the impulsive deflections can be increased until the frozen core 29 of the temperature-controlled product 1 has shrunk to a minimum volume. Subsequently, the frequency of the impulse sequence can be reduced. Alternatively, in a first portion of the temperature-control process, the maximum deflection can also be selected to be relatively small until the outer region of the temperature-controlled product has thawed and is in a liquid state. In the second part of the temperature-control process, the maximum deflection of the actuation element 12, 13 can then be increased such that the mixing within the temperature-controlled product can be increased and the thawing process can thus be accelerated. As the temperature-control process proceeds, the maximum deflection and/or the frequency and/or the acceleration can then be reduced again until the temperature-controlled product 1 has reached the desired target temperature.

In order to actuate the actuation element 12, 13, a stepper motor, an AC/DC motor having a gearing, or an electrically operated lifting/rotary magnet can also be used as an actuator, instead of an actuating motor. Alternatively, a pneumatically or hydraulically operated cylinder can also be used to actuate the actuation element 12, 13.

According to an alternative embodiment of the invention, any desired chemical substance or any desired material that is in a liquid or viscous state can also be brought to a desired temperature, instead of a frozen temperature-controlled product.

If the temperature-controlled product consists of a material having a relatively large surface area or volume, such as concrete or the like, the temperature-controlled product is deflected at multiple points on preferably opposite faces and only by means of actuation elements that are linearly moved. This results in preferably multiple points of impact on the temperature-controlled product at which the actuation elements act in a common actuation direction or in a manner offset from one another in parallel. In particular, in this case, the actuation elements can be arranged transversely offset in relation to the actuation direction thereof in a cascaded manner, wherein the actuation elements are able to be actuated in a time-staggered manner transversely to the actuation direction or to act on the temperature-controlled product.

Figure 8:
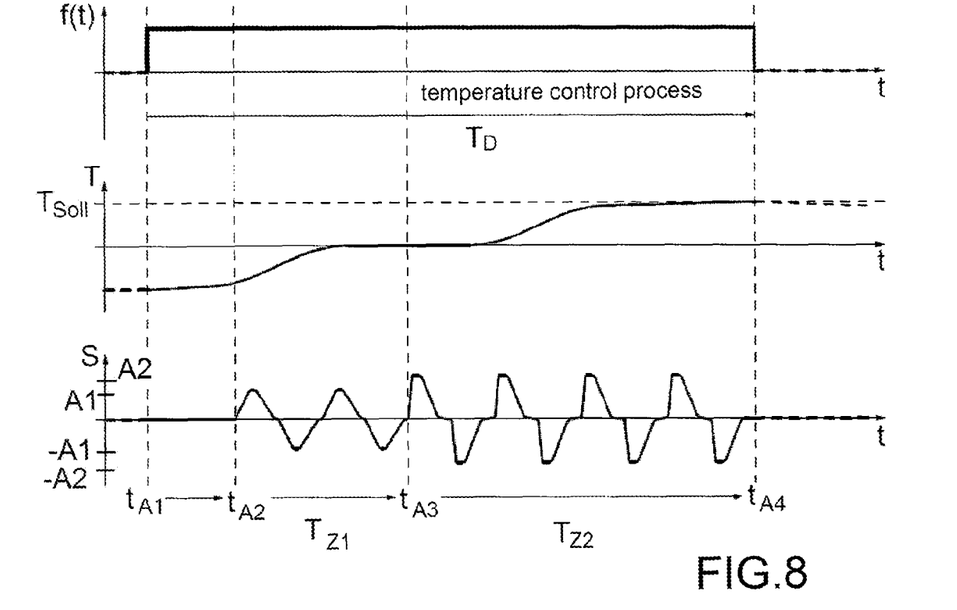
FIG. 8 is a distance/time chart according to a first example movement profile of the invention.

FIG. 8 shows a temperature-control process according to a first movement profile. Essentially, a compressive force can be exerted on part of the temperature-controlled product 1 by the actuation element 12, 13 on the basis of operating or process parameters. A duration of action, a size of action and/or an intensity of action (acceleration) of the actuation element 12, 13 can be varied during the temperature-control process.

FIG. 8 shows a movement profile for thawing a temperature-controlled product (plasma) from a frozen state into a liquid state of a specified target temperature $T_{Soll}$. In a preliminary time interval between the times $t_{A1}$ and $t_{A2}$, the temperature-controlled product 1 is still in a practically entirely frozen initial state, and no movement is yet taking place. In a first time interval $T_{Z1}$ between the times $t_{A2}$ and $t_{A3}$, part of the temperature-controlled product has already been liquefied, and the actuation element 12, 13 is periodically operated, by way of example, at a first frequency, at a first, reduced amplitude and with a first absolute slope (acceleration) such that the temperature of the temperature-controlled product 1 reaches around 0° C. The time interval $T_{Z2}$ begins at the time $t_{A3}$ and ends at the time $t_{A4}$. In comparison with the first time interval $T_{Z1}$, the actuation element 12, 13 is periodically moved, by way of example, at a larger amplitude A2 and with a second, larger absolute slope of deflection (acceleration) to the amplitude A2, but at the same frequency. The actuation of the actuation element 12, 13 is changed at a fixed specified time $t_{A3}$ or on the basis of an operating or process parameter, for example the change in load on the actuation element 12, 13, which can be identified by a change in the motor current of the actuator. The slope to the amplitude of the actuation element 12, 13 is understood to refer to the gradient of the distance curve/deflection or to the acceleration of the actuation element 12, 13, said gradient extending from zero to the amplitude A1, A2. As can be seen from the second time interval $T_{Z2}$, the absolute value of the slope of deflection to the amplitude A2 or −A2 is the largest, while the return movement to the zero line is performed with a smaller slope or smaller acceleration in absolute terms.

Figure 9:
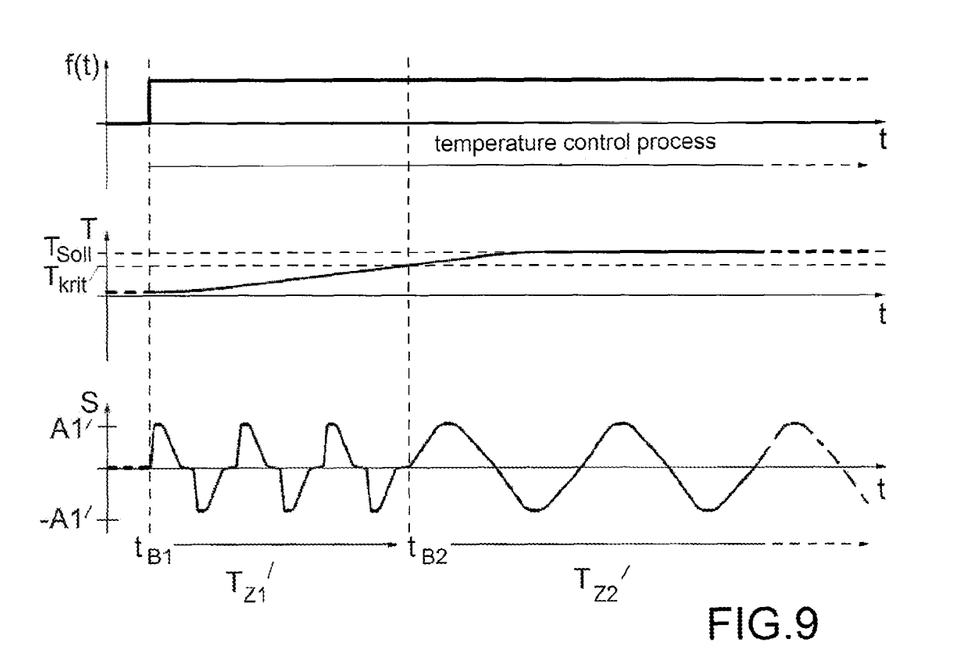
FIG. 9 is a distance/time chart according to a second example movement profile of the invention.

According to a further embodiment of a movement profile according to FIG. 9, the actuation element 12, 13 is actuated in relation to a temperature-controlled product 1 that is in a cooled but not frozen state. The temperature-controlled product 1 can be configured as a chemical additive. The temperature-controlled product 1 can therefore be in a liquid or viscous state at the beginning of the temperature-control process. The temperature-controlled product 1 is to be heated to a target temperature $T_{Soll}$. For this purpose, in a first time interval $T_{Z1}'$, which begins at the time $t_{B1}$ and ends at the time $t_{B2}$, the actuation element is periodically moved, by way of example, at a first frequency and a first amplitude and with a first absolute slope (acceleration) to the maximum deflection A1', −A1'. The movement of the actuation element 12, 13 is changed when a critical temperature $T_{krit}$ is reached, at which the temperature-controlled product 1 tends undesirably to froth up. In the second time interval $T_{Z2}'$ that then begins, the actuation element 12, 13 is moved at the same amplitude A1, −A1', but at a lower frequency and a lower acceleration or lower absolute slope to the maximum deflection A1', −A1'.

Figure 10:
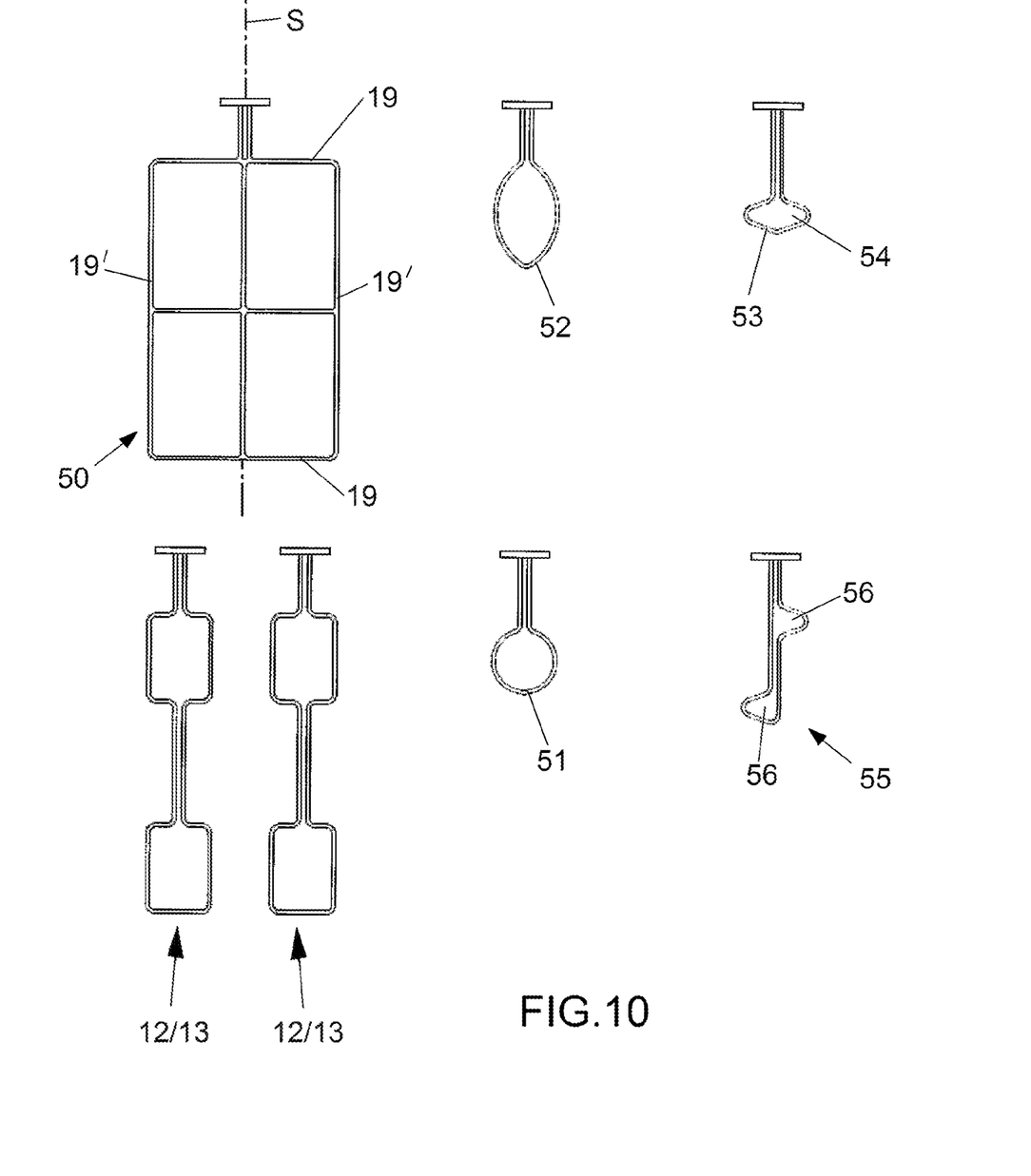
FIG. 10 is a plan view of a plurality of actuation elements.

As can be seen from FIG. 10, the actuation elements 12, 13, which are shown in FIG. 6, for example, can be arranged within the temperature-control chamber 5 one next to the other in pairs at a specified distance from one another; see bottom left in FIG. 10. Alternatively, a single actuation element 50 can also be arranged in the temperature-control chamber 5, said element having rectangular rods 19 with edge rods 19' that extend in symmetry with respect to the pivot axis S. The edge rods 19' preferably extend continuously and in straight lines over the entire length of the actuation element 50.

According to an alternative embodiment, the actuation element can also have round rods 51 (circular paddle portion) (see bottom center of FIG. 10) or elliptical rods 52 (elliptical paddle portion) (see top center of FIG. 10).

According to a further embodiment, an actuation element 53 having a diamond-shaped paddle portion 54 (see top right of FIG. 10) can be provided.

According to a further embodiment, an actuation element 55 having paddle portions 56 that are asymmetrically arranged with respect to the pivot axis S can be provided.

Depending on the dimensions of the temperature-controlled product 1, different-shaped actuation elements 12, 13, 50, 51, 53, 55 can therefore be used.

It goes without saying that the above-mentioned features can each be used individually or in groups in any desired combination. The described example embodiments are not to be understood to be an exhaustive collection, but rather are given by way of example to illustrate the invention.

LIST OF REFERENCE SIGNS 1 temperature-controlled product
2 housing
3 lid
4 base chamber
5 temperature-control chamber
6 operating elements
7 display unit
8 base
9 first heating element
10 heating module
11 upper face
12 first actuation element
13 second actuation element
14 second heating element
15, 15' faces of the temperature-controlled product
16 narrow faces
17 lower face
18 paddle portions
19, 19', 19" rods/edge rods
20 connecting rod
21 T-piece
22 holder
23 hollow cylinder
24 side wall
25 rear wall
26 front wall
27, 27' first half/second half of the paddle portion
28, 28' first half/second half of the paddle portion
29 frozen core
30 liquid
31 starting position
32 opening
40, 40', 40" wide portions
41 narrow portions
44, 44' first half/second half of a wide portion
S pivot axis
a distance
$\varphi_{MAX}$ maximum positive actuation angle
$\varphi_{MAX}$ maximum negative actuation angle
$Q_T$ transverse center plane
Φ positive angle −φ negative angle
$F_D$, $F_{D11}$, $F_{D22}$ compressive force
$F_{D21}$, $F_{D12}$ compressive force
A plane of the starting position
I motor current
$L_T$ longitudinal center plane
$b_T$ half width
T/2 half period
$S_{MAX}$, $-S_{MAX}$ maximum deflection
d1, d2 distance
d2/2 half distance
g1, g2 distance
X1 axis of symmetry
Δt1, Δt2, Δt3 period
1/T frequency
t1-t4 time
$T_{Soll}$ target temperature
$t_{41}$-$t_{44}$ times
A1, −A1, A1', −A1' deflection/amplitude
$T_{Z1}$, $T_{Z1}'$ first time interval
A2, −A2 deflection/amplitude
$T_{Z2}$, $T_{Z2}'$ second time interval
$T_{B1}$, $T_{B2}$ time
$T_{krit}$ critical temperature
50 actuation element, large design
51 actuation element, circular
52 actuation element, elliptical
53 actuation element, diamond-shaped
54 paddle portion, diamond-shaped
55 actuation element, asymmetrical
56 paddle portion, asymmetrical
$T_D$ time interval/period

The invention claimed is:

1. An apparatus for controlling a temperature of and thawing of a temperature-controlled product (1), comprising a housing (2), containing
the temperature-controlled product (1) having at least first and second faces (15, 15'),
a heating module (10) adapted for introducing heat to at least one face (15, 15') of the temperature-controlled product (1),
a mechanical actuation element (12, 13) positioned between the temperature-controlled product (1) and the heating module (10), by means of which the temperature-controlled product (1) is configured to be moved relative to the heating module,
wherein the mechanical actuation element (12, 13) is a rod element wherein rods (19, 19') surrounding an opening (32) are adapted to make direct contact with the temperature-controlled product (1) and which is configured to be actuated so as to perform a periodic and/or non-periodic movement.

2. The apparatus according to claim 1, wherein the actuation element (12, 13) is adapted to be actuated such that the actuation element (12, 13) performs a pivoting movement in relation to a pivot axis (S), wherein a space for housing is adapted to receive the temperature-controlled product (1) such that it is intersected by an orthogonal projection of the pivot axis (S) onto a longitudinal center plane ($L_T$) of said product when housed.

3. The apparatus according to claim 2, wherein the pivot axis (S) extends along a center plane of the space for housing the temperature-controlled product (1).

4. The apparatus according to claim 2, wherein the rods (19, 19') surrounding the opening (32) form a plurality of paddle portions (18) that are arranged offset along the pivot axis (S) and the rods (19, 19') have circular-shaped cross-sections.

5. The apparatus according to claim 4, wherein the housing space is designed so that the temperature-controlled product (1) is arranged in relation to the actuation element (12, 13) such that the temperature-controlled product (1) entirely or at least in part covers the paddle portion (18) of the actuation element (12, 13).

6. The apparatus according to claim 1, wherein the actuation element (12, 13) is disposed in a planar shape.

7. The apparatus according to claim 1, wherein the actuation element (12, 13) is configured to be actuated by a coupled actuator in such a way that the actuation element (12, 13) is pivoted back and forth between a maximum and minimum actuation angle ($\varphi_{MAX}$, $-\varphi_{MAX}$).

8. The apparatus according to claim 1, wherein the actuation element (12, 13) in operation is actuated so as to be continuously pivoted at a frequency of 0.1 to 25 Hz.

9. The apparatus according to claim 1, wherein the actuation element (12, 13) performs a linear movement and/or pivoting movement at an amplitude in the range of +/−2 mm to +/−100 mm.

10. The apparatus according to claim 1, wherein the at least first and second faces of the temperature-controlled product (1) are opposite to each other, wherein the actuation element (12, 13) is adapted to be in contact with each of the opposite faces (15, 15') of the temperature-controlled product (1), and wherein the actuation element (12, 13) is adapted to be actuated so as to be synchronously or asynchronously pivoted in the same rotational direction about pivot axes(S) that are arranged in parallel and offset from one another.

11. The apparatus according to claim 1, wherein the rods (19, 19', 19") of the actuation element (12, 13) consist of a wire material.

12. The apparatus according to claim 1, wherein the apparatus is adapted to the temperature-controlled product (1) such that a deflection and/or a frequency and/or an acceleration of the pivoting or a linear movement of the actuation element (12, 13) is dependent on operating or process parameters.

13. An apparatus for controlling a temperature of and thawing of a temperature-controlled product (1), comprising a housing (2), containing
a space for housing the temperature-controlled product (1) having at least first and second faces,
a heating module (10) adapted for introducing heat to at least one face (15, 15') of the temperature-controlled product (1),
a mechanical actuation element (12, 13), by means of which the temperature-controlled product (1) is configured to be moved relative to the heating module,
wherein the mechanical actuation element (12, 13) is a rod element wherein rods (19, 19') surrounding an opening (32) are adapted to make direct contact with the temperature-controlled product (1) and which is configured to be actuated so as to perform a periodic and/or non-periodic movement, wherein a resting surface area of the actuation element (12, 13) on the temperature-controlled product (1) and/or on a heating element (9, 14) is smaller than 10% of the face (15, 15') of the temperature-controlled product (1) facing the actuation element (12, 13) and/or of an upper face (11) or lower face (17) of the heating element (9, 14) facing the actuation element (12, 13).

14. A method for controlling the temperature of and thawing of a temperature-controlled product (1), comprising
introducing heat from a heat module to the temperature-controlled product (1) while a compressive force ($F_{D11}$, $F_{D12}$, $F_{D21}$, $F_{D22}$) is exerted on part of the temperature-controlled product (1) in a specified time interval ($T_D$) by means of an actuation element (12, 13, 50, 51, 52, 53, 55) moving relative to the heat module, wherein the actuation element is a mechanical actuation element (12, 13) positioned between the temperature-controlled product (1) and the heating module (10), by means of which the temperature-controlled product (1) is configured to be moved relative to the heating module, wherein the mechanical actuation element (12, 13) is a rod element wherein rods (19, 19') surrounding an opening (32) are adapted to make direct contact with the temperature-controlled product (1) and which is configured to be actuated so as to perform a periodic and/or non-periodic movement, and changing a duration of action, a size of action and/or an intensity of action of the actuation element (12, 13, 50, 51, 52, 53, 55) on the basis of a specified point in time of a temperature-control process ($T_D$) and/or an operating or process parameter of the temperature-controlled product (1).

15. The method according to claim 14, wherein the actuation element (12, 13, 50, 51, 52, 53, 55) periodically and/or non-periodically acts on the temperature-controlled product (1) from opposite sides thereof, wherein the acting compressive force ($F_{D11}$, $F_{D22}$, $F_{D21}$, $F_{D12}$) extends on a common straight line in an opposite direction, and wherein the compressive force ($F_{D11}$, $F_{D22}$, $F_{D21}$, $F_{D12}$) has the highest value at the same point in time.

16. The method according to claim 14, wherein in a first time interval ($T_{Z1}$), the actuation element (12, 13) is periodically and/or non-periodically moved at a first frequency and at a first amplitude (A1, −A1) and at a first acceleration, and at a time ($t_{43}$), in that the first time interval ($T_{Z1}$) is ended on the basis of a specified period ($T_{Z1}$) or on the basis of an operating or process parameter of the actuation element (12, 13), and in that, in a subsequent second interval ($T_{Z2}$), the actuation element (12, 13) is periodically and/or non-periodically operated at a second frequency that is the same as the first frequency, at a second amplitude (A2, −A2) that is smaller than the first amplitude, and at an acceleration that is smaller than the acceleration in the first time interval ($T_{Z1}$) in absolute terms.

17. The method according to claim 14, wherein in a first time interval ($T_{Z1}'$), the actuation element (12, 13) is periodically and/or non-periodically moved at a first frequency, at a first amplitude (A1', −A1') and at a first acceleration, and in that when a specified critical temperature ($T_{krit}$) of the temperature-controlled product (1) is reached, the actuation element (12, 13) is periodically and/or non-periodically operated, in a second time interval ($T_{Z2}'$), at a second frequency that is lower than the first frequency, at a second amplitude (A2, −A2) that is the same as the first amplitude (A1', −A1'), and at an acceleration that is lower than the acceleration in the first time interval ($T_{Z1}'$).

18. The method according to claim 14, wherein the actuation element (12, 13) is moved individually with regard to a frequency, an amplitude and an acceleration on the basis of fixed specified and/or current operating or process parameters at any desired times and for any desired time intervals $T_Z$.

* * * * *